US007474923B2

(12) United States Patent
Houben et al.

(10) Patent No.: US 7,474,923 B2
(45) Date of Patent: Jan. 6, 2009

(54) MICRO ELECTROMECHANICAL SWITCHES AND MEDICAL DEVICES INCORPORATING SAME

(75) Inventors: Richard P. M. Houben, Lanaken (BE); Henri G. M. Heynen, Lower Templestowe (AU)

(73) Assignee: Medtronic, Inc., Minneapolis, MN (US)

(*) Notice: Subject to any disclaimer, the term of this patent is extended or adjusted under 35 U.S.C. 154(b) by 309 days.

(21) Appl. No.: 10/425,527

(22) Filed: Apr. 29, 2003

(65) Prior Publication Data

US 2004/0220650 A1 Nov. 4, 2004

(51) Int. Cl.
*A61N 1/05* (2006.01)

(52) U.S. Cl. .......................... 607/37; 607/119; 439/909

(58) Field of Classification Search ............ 607/36–39, 607/119; 439/909
See application file for complete search history.

(56) References Cited

U.S. PATENT DOCUMENTS 3,678,438 A * 7/1972 Gamson ..................... 439/445
4,078,183 A * 3/1978 Lewiner et al. ............. 307/112
4,712,555 A 12/1987 Thornander et al. .... 128/419 PG
5,312,453 A 5/1994 Shelton et al.
5,398,011 A * 3/1995 Kimura et al. ................ 335/79
5,475,353 A * 12/1995 Roshen et al. ................ 335/78
5,522,865 A 6/1996 Schulman et al. ............. 607/56
5,662,692 A 9/1997 Paspa et al.
5,674,259 A 10/1997 Gray
5,797,970 A 8/1998 Pouvreau
5,847,631 A * 12/1998 Taylor et al. .................. 335/78
5,994,816 A * 11/1999 Dhuler et al. ............... 310/307
6,038,480 A * 3/2000 Hrdlicka et al. ............. 607/116
6,125,300 A * 9/2000 Weijand et al. ............... 607/66
6,303,885 B1 10/2001 Hichwa et al.
6,366,186 B1 * 4/2002 Hill et al. ....................... 335/78
6,535,766 B1 3/2003 Thompson et al.
6,804,552 B2 10/2004 Thompson et al.

* cited by examiner

*Primary Examiner*—George R Evanisko
*Assistant Examiner*—Michael Kahelin
(74) *Attorney, Agent, or Firm*—Michael C. Soldner

(57) ABSTRACT

An apparatus for conducting electrical energy to a part of the body (e.g. the heart) and/or for providing sensor data from the body to a device suitably includes an input lead configured to electrically interface with a medical device. A switch electrically coupled to the input lead includes first and second output terminals and a switching input that is responsive to a control signal. The switch toggles electrical energy between first and second output leads in response to the control signal to provide energy to a particular location on the part of the body. The various electromechanical switches described herein may be useful in a wide variety of applications, including many applications in the medical device field. Such switches may be useful in producing Y-adapter-type lead multiplexers for implantable devices, for example, as well as in producing switchable electrode arrays, sensor leads and the like.

8 Claims, 10 Drawing Sheets

MICRO ELECTROMECHANICAL SWITCHES AND MEDICAL DEVICES INCORPORATING SAME

CROSS-REFERENCE TO RELATED APPLICATION

Cross-reference is hereby made to commonly assigned related U.S. Application, filed concurrently herewith, Ser. No. 10/425,861, entitled "Multi-Stable Micro Electromechanical Switches and Methods of Fabricating Same", incorporated herein by reference in its entirety.

TECHNICAL FIELD

The present invention generally relates to electromechanical switches, and more particularly relates to applications of electromechanical switches, particularly in the medical device field.

BACKGROUND

Switches are commonly found in most modern electrical and electronic devices to selectively place electrical, optical and/or other signals onto desired signal paths. Switches may be used to enable or disable certain components or circuits operating within a system, for example, or may be used to route communications signals from a sender to a receiver. Electromechanical switches in particular are often found in medical, industrial, aerospace, consumer electronics and other settings.

In recent years, advances in micro electromechanical systems (MEMS) and other technologies have enabled new generations of electromechanical switches that are extremely small (e.g. on the order of micrometers, or $10^{-6}$ meters) in size. Because many micro switches can be fabricated on a single wafer or substrate, elaborate switching circuits may be constructed within a relatively small physical space. Although it would generally be desirable to include such tiny electromagnetic switches in medical devices (e.g. pacemakers, defibrillators, etc.) and other applications, several disadvantages have prevented widespread use in many products and environments. Most notably, many conventional micro electromechanical switches consume too much power for practical use in demanding environments, such as in a device that is implanted within a human body. Moreover, difficulties often arise in isolating the switch actuation signal from the transmitted signal in such environments. Further, the amount of energy (e.g. electrical voltage) typically required to actuate a conventional electromechanical switch may be too great for many practical applications, particularly in the medical field.

More recently, however, several new switch designs have come to light that reduce or eliminate the disadvantages commonly found in the prior art. Accordingly, it is desirable to build medical devices and the like that incorporate micro electromechanical switch designs that consume relatively low amounts of power, and that can be actuated with a relatively small amount of energy. In particular, it is desirable to build Y-adapters and/or electrode array devices that incorporate electromagnetic switches. Furthermore, other desirable features and characteristics of the present invention will become apparent from the subsequent detailed description and the appended claims, taken in conjunction with the accompanying drawings and the foregoing technical field and background.

BRIEF SUMMARY

In one aspect, a device or apparatus for conducting electrical energy to a part of the body (e.g. the heart) and/or for providing sensor data from the body suitably includes an input lead configured to electrically interface with an energy source and to receive the electrical energy therefrom. The energy source may be a pacemaker, defibrillator, implantable medical device or the like. A switch electrically coupled to the input lead suitably includes first and second output terminals and a switching input that is responsive to a control signal. The switch toggles electrical energy between at least first and second output leads in response to the control signal to provide the energy to or from a particular location on the part of the body. The various electromechanical switches described herein may be useful in a wide variety of applications, including many applications in the medical device field. Such switches may be useful in producing Y-adapter-type lead multiplexers for implantable electrode arrays and the like.

BRIEF DESCRIPTION OF THE DRAWING FIGURES

The present invention will hereinafter be described in conjunction with the following drawing figures, wherein like numerals denote like elements, and FIGS. 1A-B are cross-sectional side views of exemplary opposing contact members of an exemplary switch;

FIGS. 2A-D are cross-sectional side views illustrating an exemplary process for producing exemplary contact members;

Figure 5A:
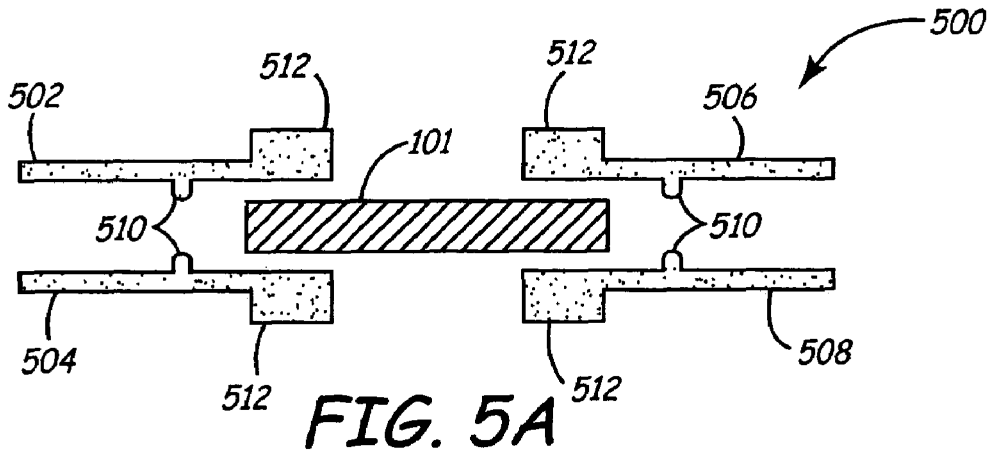
Figure 5B:
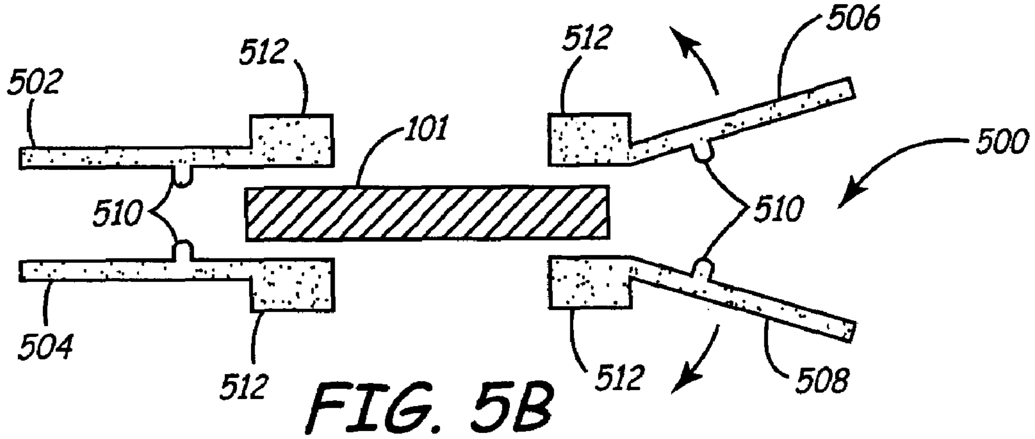
Figure 5C:
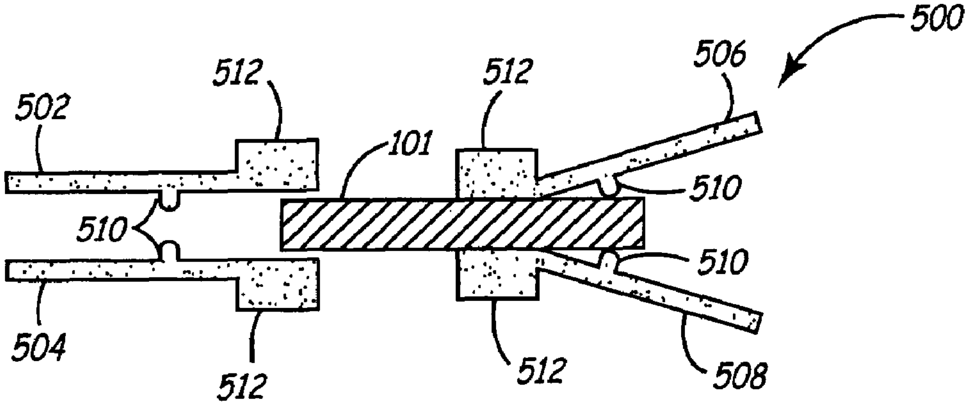
Figure 6:
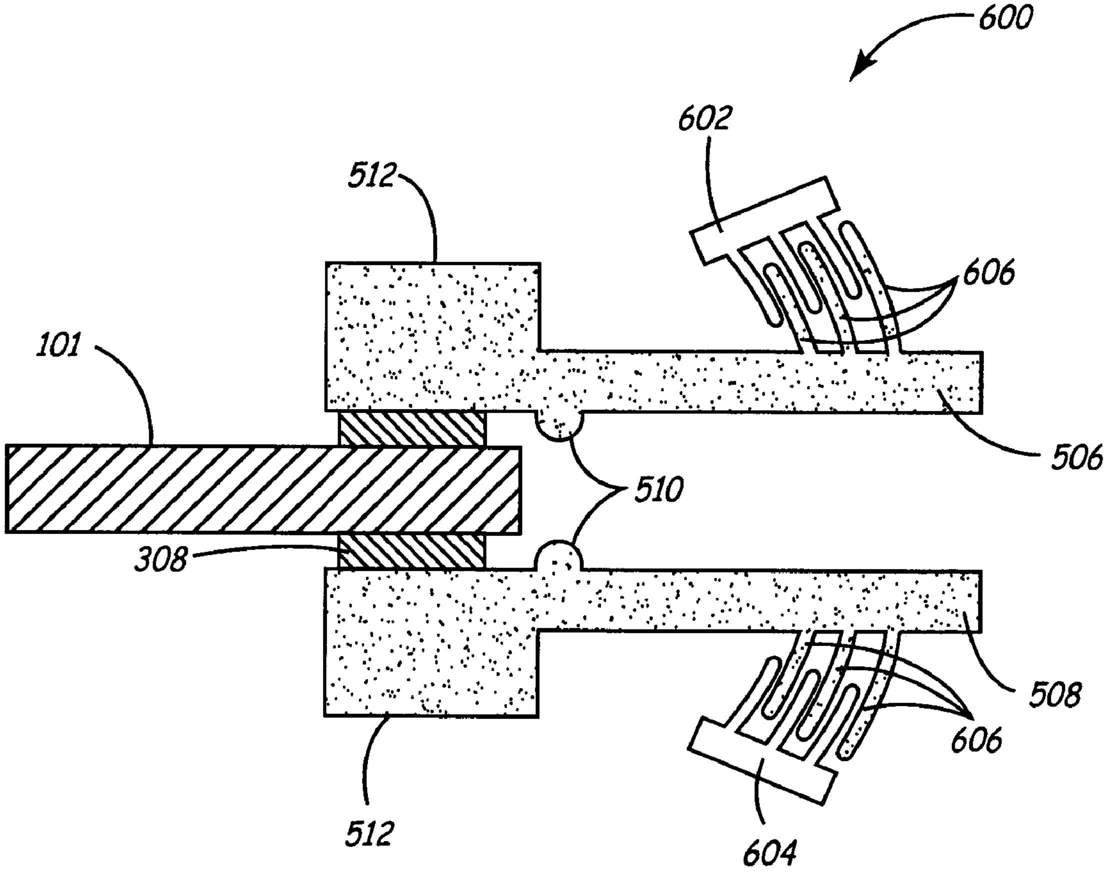
Figure 7A:
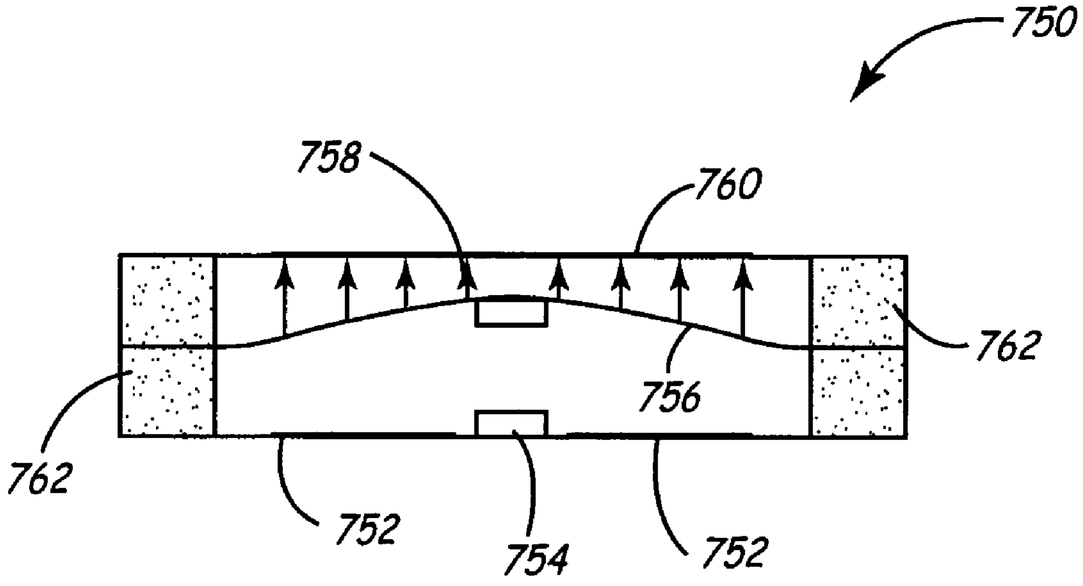
Figure 7B:
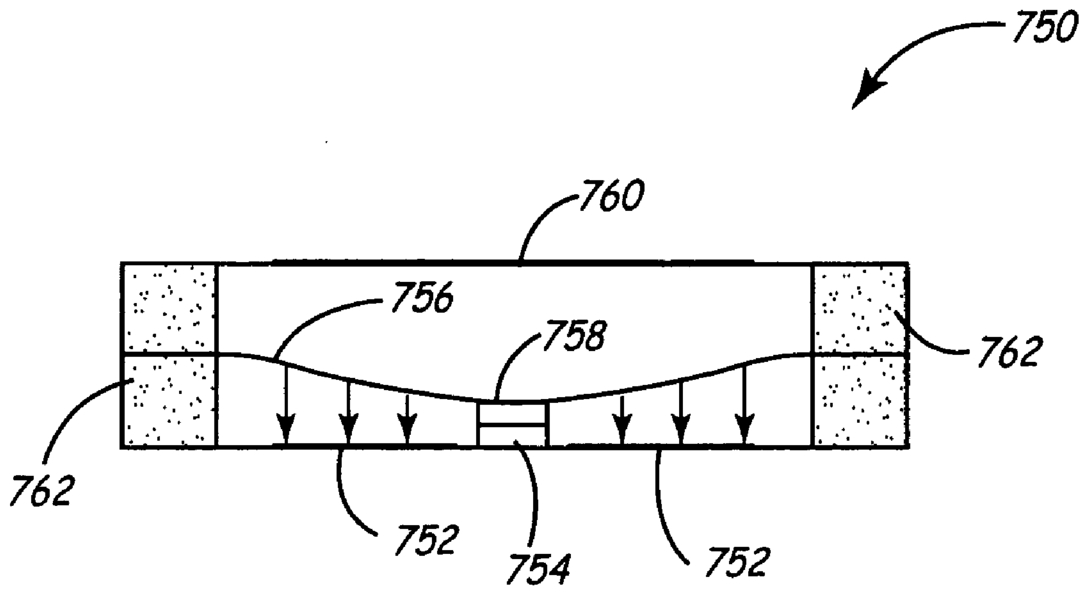
Figure 8:
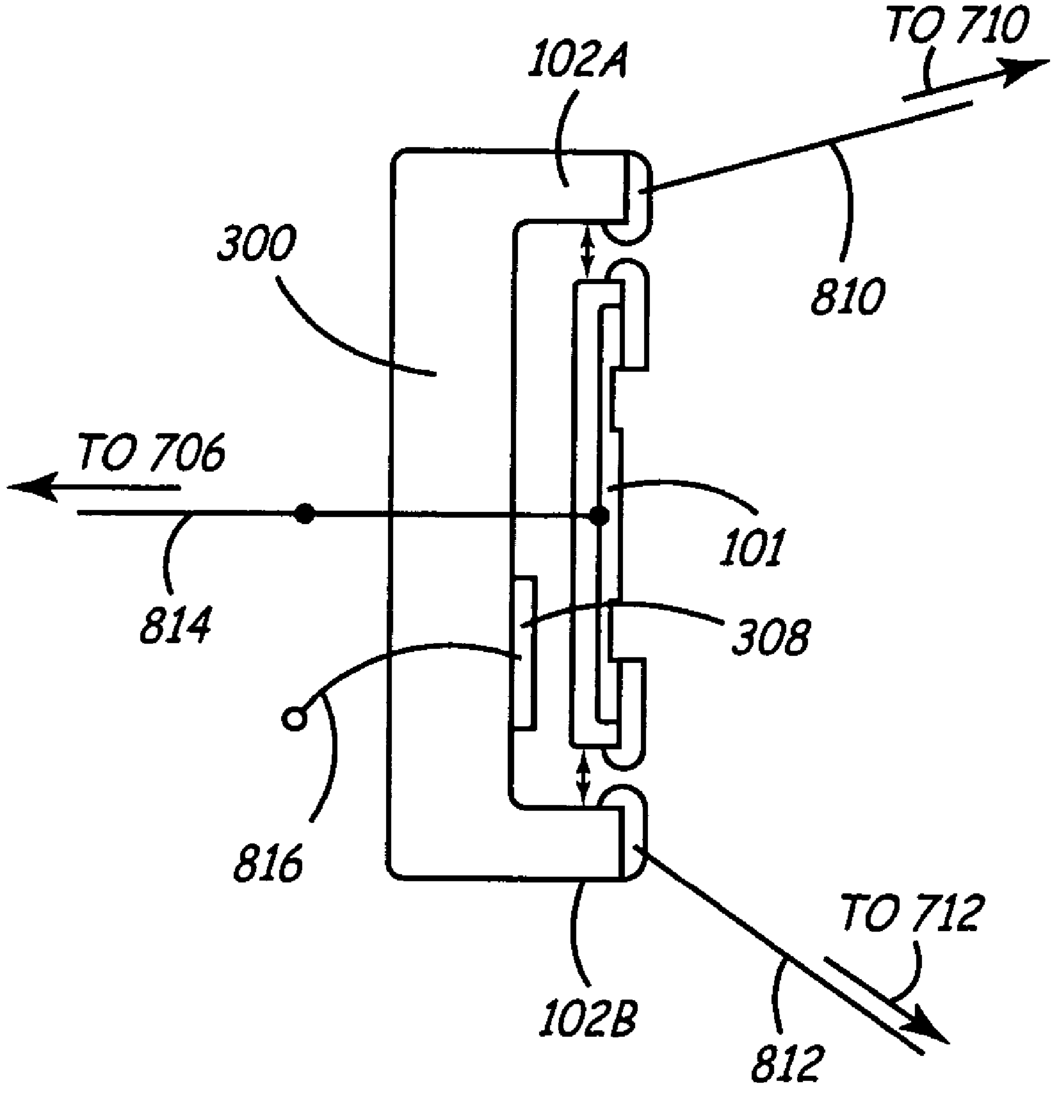
Figure 9:
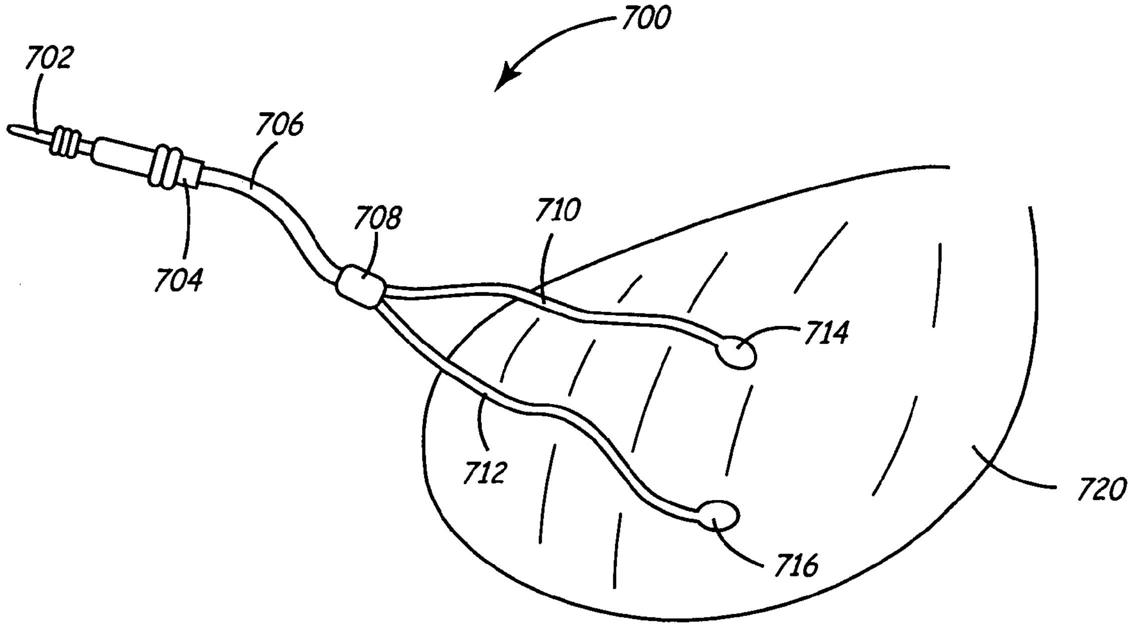
Figure 10:
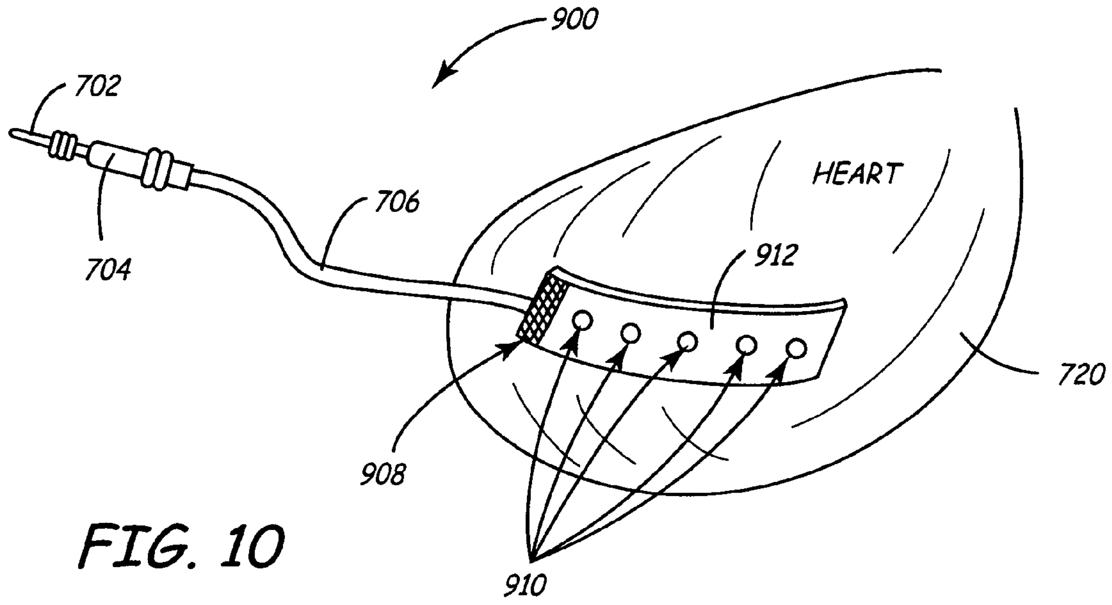
Figure 11:
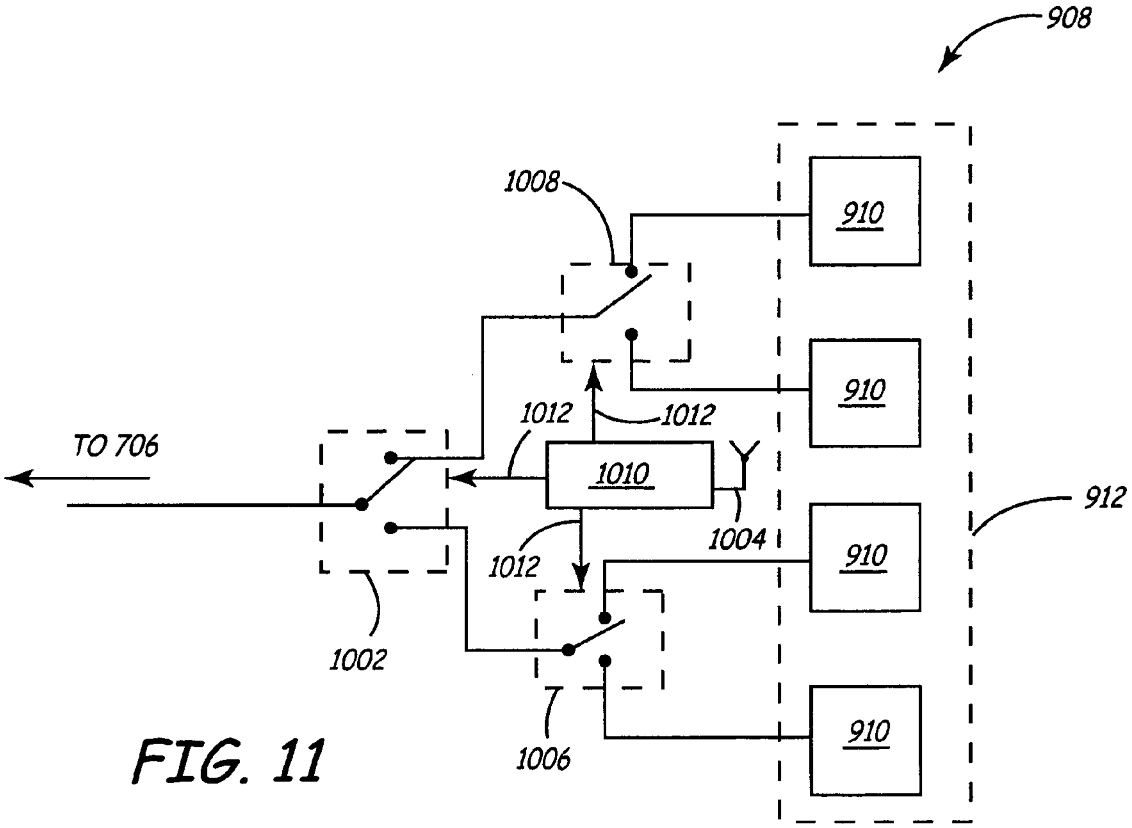

FIGS. 5A-C are top views of an exemplary tri-stable micro electromechanical switch;

FIG. 6 is a top view of an exemplary bi-stable micro electromechanical switch with an exemplary actuating circuit;

FIGS. 7A-B are top views of an exemplary bi-stable micro electromechanical switch with a buckling membrane;

FIG. 8 is a top view of an exemplary micro-electromechanical switch with output terminals configured to be connected to electrical leads;

FIG. 9 is a perspective view of an exemplary Y-adapter for use with a human heart;

FIG. 10 is a perspective view of an exemplary switch array for use with a human heart; and FIG. 11 is a schematic diagram of an exemplary switch array.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

According to various exemplary embodiments, switches suitable for use in medical devices and the like are fabricated using conventional MEMS techniques. The switches suitably include a moveable armature, cantilever or other member that is capable of selectively engaging one or more receiving terminals to place the switch into a desired state. In various embodiments, the moveable member and/or receiving terminal(s) are fashioned with a protruding region formed of gold or another conductive material to improve electrical connections within the switch. In further embodiments, the switch is configured to exhibit two or more stable output states without consuming energy to maintain the switch in a desired state. Stability is provided by mechanically biasing one or more receiving terminals to a position corresponding to a first state of the switch (e.g. an open state corresponding to an open circuit), and by positioning the moveable member into the bias position when the switch is in another state (e.g. corresponding to a closed switch). In such embodiments the mechanical bias of the receiving terminals maintains contact with the moveable member even when the energy used to displace switch components is removed. Accordingly, the switch remains in the desired state without requiring continuous application of energy, thereby conserving power. The various switches described herein may be used in a wide variety of applications, including applications in the medical, industrial, aerospace, consumer electronic or other arts. Several applications in the medical field include switchable Y-adapter lead multiplexers for implantable medical devices, switchable electrode arrays, and the like.

Figure 1A:
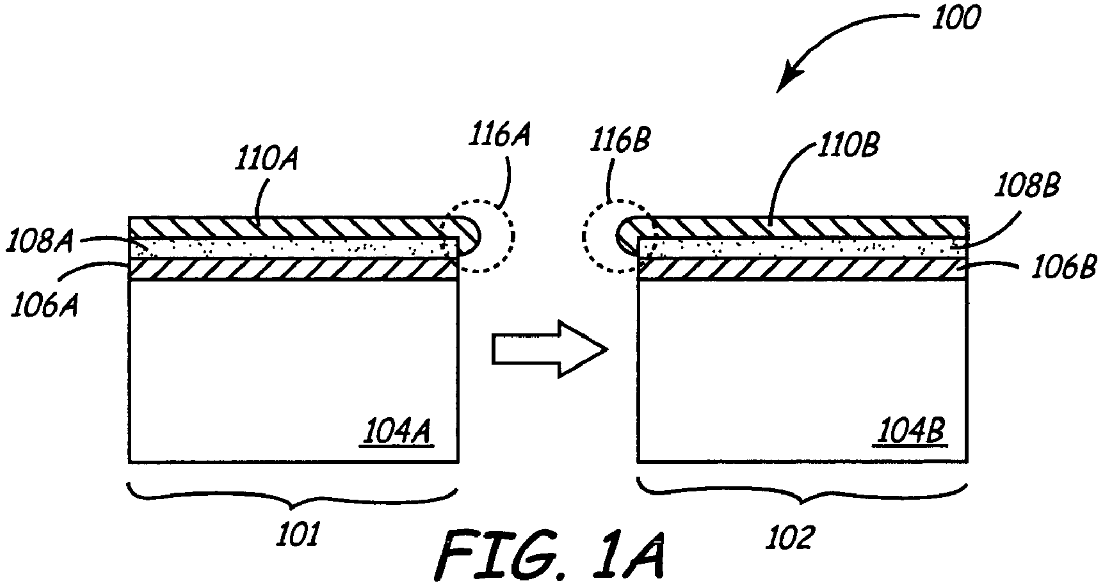

With reference now to FIG. 1A, an exemplary electromechanical switch suitably includes a moveable member 101 that electrically contacts with one or more receiving terminals 102 to complete an electrical circuit, and to thereby place switch 100 into a desired output state (e.g. open or closed). Moveable member 101 and any associated terminals 102 are collectively referred to herein as "contact members". Moveable member 101 is suitably formed from a substrate layer 104A, an insulating layer 106A, a conducting layer 108A, and a conductive coating 110A that appropriately surrounds conducting layer 108A to form a protruding region 116A that extends radially outward from substrate 104A, and that provides an appropriate electrical contact to receiving terminal 102. Similarly, terminal 102 is suitably formed from a substrate layer 104B, an insulating layer 106B, a conducting layer 108B, and a conductive coating 110B. Conductive coating 110B may also be formed to create a protruding region 116B extending outward from receiving terminal 102 to interface with protruding region 116A of moveable member 101 and to thereby form an electrical connection to close switch 100. Although both moveable member 101 and terminal 102 are both shown in FIG. 1 A with protruding regions 116, the protruding portion may be removed from either of the contact members in various alternate embodiments.

Figure 1B:
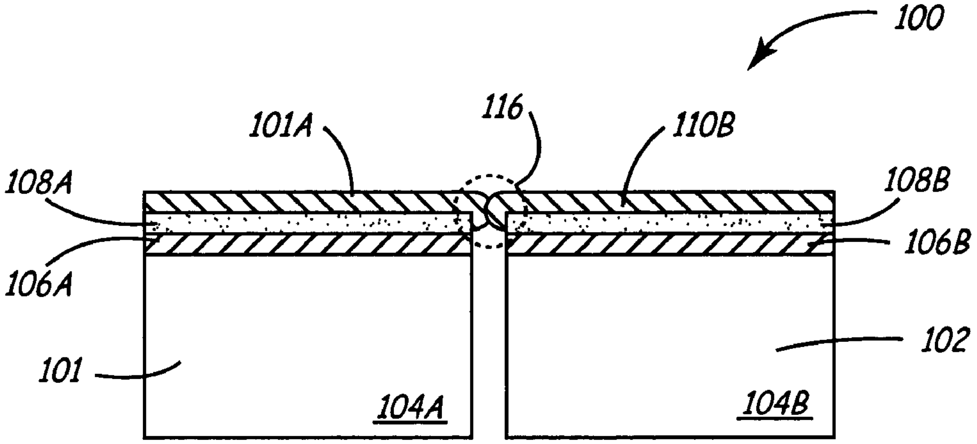

In operation, moveable member 101 is capable of lateral movement to switchably engage receiving terminal 102. FIG.1 B shows an exemplary switch 100 wherein moveable member 101 is in contact with terminal 102 to thereby complete an electrical circuit and to place switch 100 into a "closed" state. Because protruding regions 116 extend outward from substrate 104, protruding regions 116 appropriately form an electrical connection without requiring contact between substrate layers 104A-B and/or insulating layers 106A-B. This separation between the non-conducting layers of moveable member 101 and terminal 102 provides an electrical isolation between the two members, which in turn assists in isolating actuation signals propagating in switch 100 from signals transmitted by switch 100, as described more fully below.

Figure 2A:
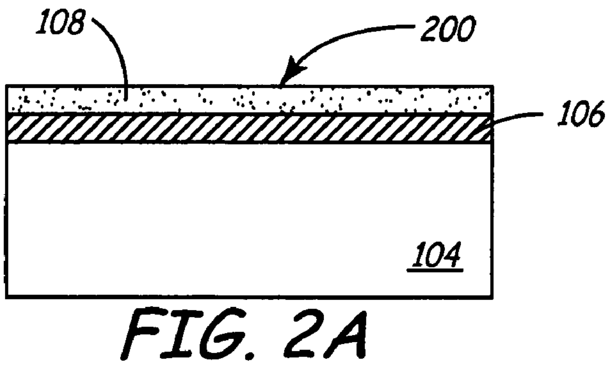
Figure 2B:
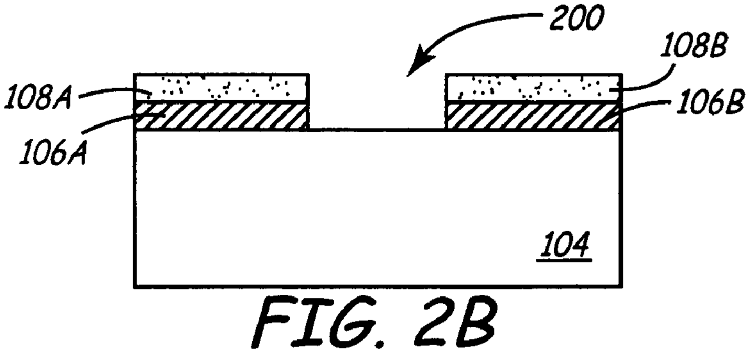
Figure 2C:
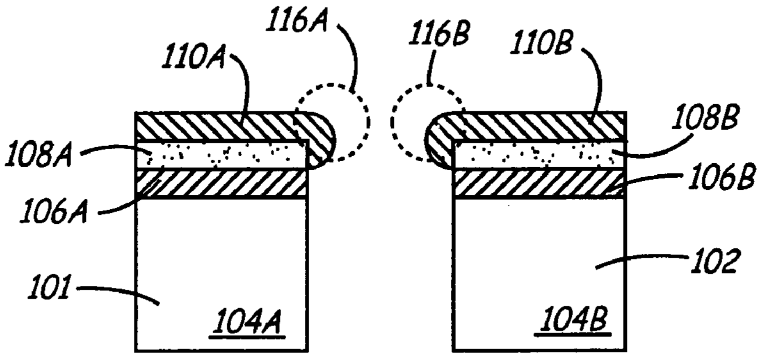
Figure 2D:
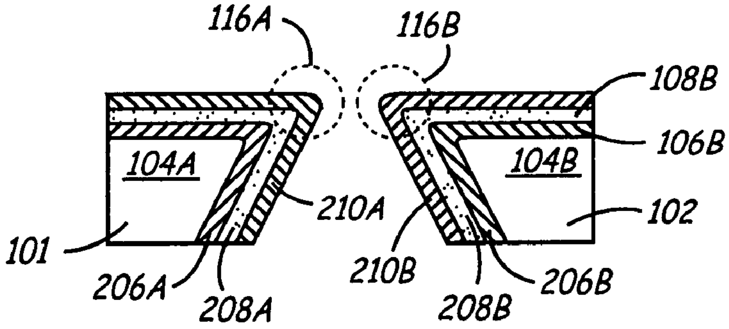

Referring now to FIGS. 2A-2D, an exemplary process for building a switch 100 suitably includes the broad steps of forming insulating and conducting layers on a substrate (FIG. 2A), isolating the moveable members and terminals (FIG. 2B), applying a conductive coating to the appropriate portions of the switch (FIG. 2C), and optionally etching or otherwise processing a backside of the substrate to further define terminals, moveable members and the like (FIG. 2D). The various steps described in the figures may be implemented using any manufacturing or fabrication techniques, such as those conventionally used for MEMS and/or integrated circuit technologies. Various switch fabrication techniques are described, for example, in U.S. Pat. No. 6,303,885.

With reference to FIG. 2A, the switch fabrication process suitably begins by preparing a substrate assembly 200 that includes a substrate 104, an insulating layer 106 and a conducting layer. Substrate 104 is any material such as glass, plastic, silicon or the like that is capable of supporting one or more switches 100. In an exemplary embodiment, substrate 104 is formed from doped silicon, and has a thickness on the order of 35-76 micrometers, although the actual dimensions will vary widely from embodiment to embodiment. Similarly, the optional dopants provided in substrate 104 may be selected to improve the connectivity of the switch, and will also vary widely with various embodiments. Substrate 104 may be prepared in any manner, and in an exemplary embodiment is prepared using conventional Silicon-on-Insulator (SOI) techniques. Insulating layer 106 may be formed of any electrically insulating material such as glass, silicon oxide, or the like, and may be placed on or near an exposed surface of substrate 104 using any technique such as sputtering, deposition or the like. Similarly, conducting layer 108 may be any metal such as aluminum, copper, gold or silver, and may be placed according to any technique. In an exemplary embodiment, insulating layer 106 and conducting layer 108 are deposited on substrate 104 using conventional liquid-phase epitaxy and/or low pressure chemical vapor deposition techniques, as appropriate.

With reference to FIG. 2B, the various electrically conducting and insulating regions of switch 100 may be suitably isolated in substrate assembly 200. Conducting layer 108 may be patterned or otherwise processed using conventional etching, lithography or other techniques, for example, to create gaps 201 between separate electrical nodes. Patterning appropriately delineates moveable members 101, actuating circuitry, receiving terminals 102 and the like from each other. An exemplary pattern for a switch 100 is discussed below in conjunction with FIG. 3. In alternate embodiments, conducting layer 108 may be eliminated entirely, with conducting and/or insulating regions on substrate assembly 200 provided by selective doping of substrate 104, as described more fully below.

Referring now to FIG. 2C, an additional conducting layer 110 of gold or another appropriate material may be grown, electroplated or otherwise formed on conducting layer 108. In one embodiment, substrate assembly 200 is further formed with an additional non-conducting layer of oxide or the like that is applied after etching or patterning. Electroless gold or another conductor can then be "grown" or otherwise applied on portions of substrate assembly that are unprotected by the additional non-conducting layer. Alternatively, conductive material can be evaporated or sputtered selectively on conductive areas using a shadow mask or the like. In yet another embodiment, gold or another conductive material is suitably electroplated, as described in conjunction with FIG. 3 below. In such embodiments conducting layer 108 may not be present, with silicon dioxide or another insulating material providing electrical insulation between parts of switch 100 used for electrostatic actuation and parts used for signal conduction. In various embodiments, protruding region 116 is formed of conductive material as appropriate to engage other contact members while maintaining electrical isolation between substrate portions 104. Protruding regions 116 may be formed as a consequence of the additional exposed surface near the corners of conducting layer 108, for example, or by any other technique.

In a further embodiment, the various components of switch 100 may be physically separated from each other using conventional MEMS techniques. An anisotropic etchant such as Tetra-Methyl Ammonium Hydrate (TMAH) or Potassium Hydroxide (KOH), for example, may be used to separate moveable member 101 from terminal 102 as appropriate. In further embodiments (and as shown in FIG. 2D), additional insulating layers 206A,B and/or conducting layers 208A,B may be formed after separation but before formation of the outer conducting layer 110 to improve coverage by layer 110/210A-B. Such layers may be formed following additional etching or processing from the front or back side of substrate 104, as appropriate. Accordingly, the various contact members and other components of switch 100 may take any shape or form in a wide variety of alternate but equivalent embodiments.

Figure 3:
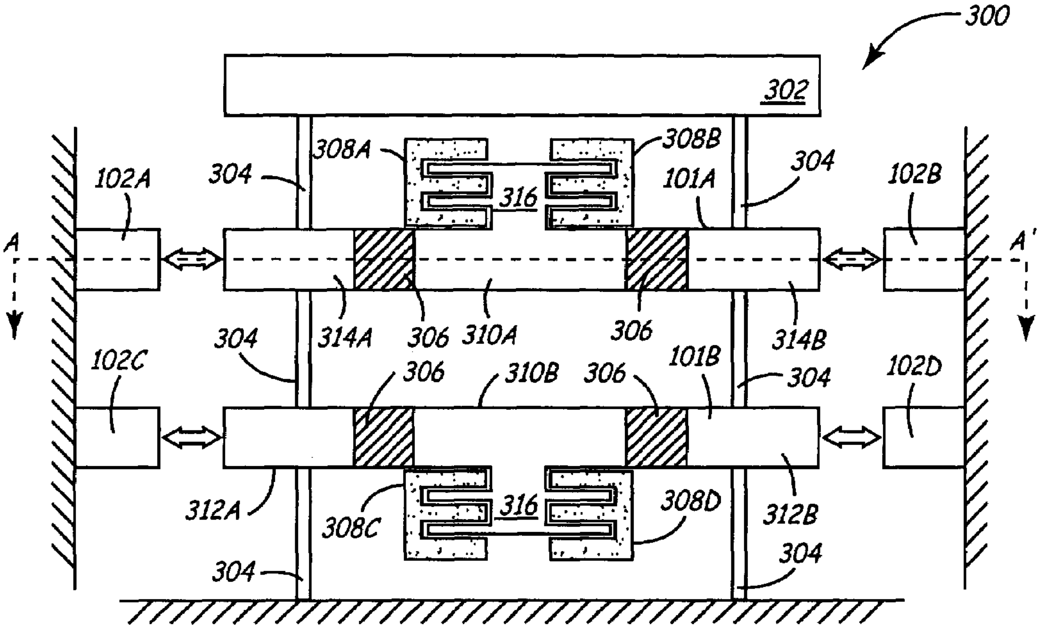
FIG. 3 is a top view of an exemplary electromechanical switch.
Figure 4:
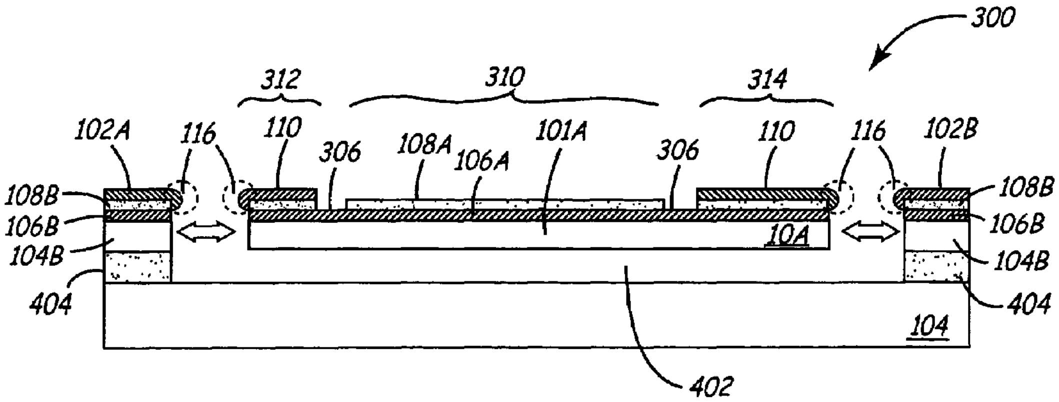
FIG. 4 is a side view of an exemplary electromechanical switch.

FIGS. 3 and 4 are top and side views, respectively, of an exemplary switch assembly 300, with FIG. 4 being a cross-sectional side view taken along line A-A' in FIG. 3. Referring now to FIG. 3, an exemplary switch assembly 300 suitably includes one or more cantilevers or other moveable members 101A-B that are capable of interacting with any number of receiving terminals 102A-D, as appropriate. In the exemplary switch assembly 300 shown in FIG. 3, two tri-stable switches corresponding to moveable members 101 A and 101 B are shown. One switch, for example, has a first state corresponding to contact between moveable member 101A and terminal 102A, a second state corresponding to contact between moveable member 101A and terminal 102B, and a third state corresponding to no contact between moveable member 101A and either terminal. Similarly, the other switch shown has a first state corresponding to contact between moveable member 101B and terminal 102C, a second state corresponding to contact between moveable member 101B and terminal 102D, and a third state corresponding to no contact between moveable member 101B and either terminal. Accordingly, each of the two switches are capable of three separate output states. Alternate embodiments of switch assembly 300 may include any number of moveable members 101 and/or terminals 102. Similarly, each switch may have any number of available output states such as two, three or more.

Each moveable member 101 and terminal 102 may be formed from a common substrate 104 as described above, with one or more hinges 304 providing flexible mechanical support for each moveable member 101. Each moveable member 101A-B suitably includes two conducting regions 312 and 314 that are capable of electrically interfacing with terminals 102A-D as described above. In the exemplary embodiment shown in FIG. 3, member 101A has a first conducting region 314A that interfaces with terminal 102A and a second conducting region 314B that interfaces with terminal 102B. Similarly, member 101 B has a first conducting region 312A that interfaces with terminal 102C and a second conducting region 312B that interfaces with terminal 102D.

Each moveable member 101 may also include another conducting region 310 that may be used to actuate the member 101 between the various states of switch 300. In the exemplary embodiment shown in FIG. 3, for example, each conducting region 310 is integrally formed with a comb-type portion 316 that is sensitive to electrostatic energy or other stimulus provided by actuators 308A-D. In the exemplary embodiment shown in FIG. 3, each portion 316 includes a series of comb-like teeth that include metal, permalloy or other material capable of being actuated by one or more actuators 308A-D. In practice, each moveable member 101 may include multiple portions 316 that are sensitive to electrostatic force, and portions 316 may take any shape and/or may be located at any point on or near moveable member 101. Although not shown in FIG. 3 for purposes of simplicity, in practice each member 101 may include two or more portions 316 on opposing sides of conducting region 310, for example, to increase the response to applied electrostatic force and to thereby more easily actuate the member between the various states of switch 300.

In practice, each moveable member 101 is displaced by one or more actuating circuits 308A-D as appropriate. In the exemplary embodiment shown in FIG. 3, for example, moveable member is suitably displaced toward terminal 102A by providing an electrostatic charge on actuator 308A that attracts comb portion 316. Similarly, an electrostatic charge provided by actuator 308B appropriately attracts comb portion 316 toward terminal 102B. Providing an electrostatic charge to both actuators 308A-B appropriately attracts comb portion 316 to the central location such that member 101A is electrically separated from each terminal 102A and 102B to place the switch into an open circuit-type state. Similar logic could be applied to member 101 B, which is appropriately displaced between the three states by actuators 308C and 308D. In alternate embodiments, electrostatic attraction could be replaced or supplemented with electrostatic repulsion, RF signals, inductance of electromagnetic signals, or any other actuating force.

As briefly mentioned above, the various conducting regions 310, 312 and 314 are appropriately isolated from each other by electrically insulating portions 306, which may be exposed portions of insulating layer 106 discussed above, or which may be made up of an additionally-applied insulating material. Alternatively, insulating portions 306 (as well as some or all of the conducting portions on switch assembly 300) may be formed by injecting or otherwise placing dopant materials in the appropriate regions of substrate 104. In practice, hinges 304 and conducting regions 312 and 314 may be laid out on substrate 104 (FIGS. 1 and 4) in a pattern that allows for convenient electroplating. In such embodiments, an electrical charge applied at contact 302 has electrical continuity through conducting layer 108 (FIGS. 1-2) across each hinge 304 and conducting region 312 and 314. When such a charge is applied, outer conducting layer 110 can be readily electroplated to the desired locations on switch 300, as appropriate. Insulating regions 306 suitably provide electrical isolation for those parts of switch 300 that are not desired to become electroplated, thereby improving the manufacturability of switch 300. Electroplating may also provide appropriate protruding regions 116 as described above, and as best seen in FIG. 4.

Electroplating hinges 304 also provides mechanical reinforcement for supporting moveable members 101, which are appropriately otherwise isolated from substrate 104 to promote ease of movement. With reference now to FIG. 4, member 101A is suitably separated from substrate 104 by a gap 402 to permit lateral movement toward terminals 102A and 102B as appropriate. Gap 402 may be formed through conventional MEMS techniques, including backside etching or the like. Alternatively, substrate 104 may be formed with a sacrificial layer 404 that can be etched using conventional front side etching or otherwise removed to form gap 402. In such embodiments, sacrificial layer 402 may be formed of an oxide (e.g. silicon oxide) or another material that may be etched through cavities formed in layers 106, 108 and/or 110 as appropriate.

With reference now to FIGS. 5A-C, switch 500 is appropriately held in a number of stable output states through the use of mechanical energy applied by one or more receiving terminals. Switch 500 suitably includes at least one moveable member 101 that is displaceable to interface with one or more terminal arms 502, 504, 506, 508. Each terminal arm 502, 504, 506, 508 is appropriately designed to be moveable, rotatable, deformable or otherwise displaceable to place switch 500 into different output states. In an exemplary embodiment, each arm 502, 504, 506, 508 is designed to bend in an elastic-type fashion about a fixed point 512. Such deformabililty or elasticity may be provided by conventional MEMS or other techniques. In various embodiments, one or more terminal arms are designed to include an outcropping 510 that is able to electrically communicate with moveable member 101. In the embodiment shown in FIGS. 5A-C, terminal arms 502 and 504 cooperate to provide an electrical connection with moveable member 101 when the switch is in a first state, and terminal arms 506 and 508 cooperate to provide an electrical connection with moveable member 101 when the switch is in a second state, as shown in FIG. 5C. A third state may be provided when moveable member 101 is electrically isolated from both sets of terminal arms, as shown in FIG. 5A. The layout and structural components of switch 500 appropriately corresponds to those of switches 100, 300 and the like discussed above, or the concepts described with respect to switch 500 may be applied to any type of switch or switch architecture in a wide array of equivalent embodiments. Various equivalent embodiments of switch 500 include any number of moveable members 101, terminal arms, terminals, or output states for each moveable member 101. Although not visible in FIG. 5, each outcropping 510 or any other portion of terminal arms 502, 504, 506 and/or 508 may include a protruding region 116 as discussed above to further improve electrical connectivity between the terminal arm and moveable member 101.

Referring to FIG. 5A, switch 500 is shown in an exemplary "open" state (corresponding to an open circuit) whereby moveable member 101 is not electrically coupled to either set of terminal arms. Terminal arms 502, 504, 506 and 508 are appropriately designed such that their natural "biased" state corresponds to the open state wherein the arms are isolated from moveable member 101. As used herein, "biased state" refers to the physical space occupied by one or more terminal arms 502, 504, 506, 508 when no actuation force or energy is applied and when no other object blocks or prevents natural movement of the terminal arm.

In operation, switch 500 is placed into a different state when moveable member 101 is moved into the bias position of one or more terminal arms such that the mechanical force applied by the terminal arm in attempting to return to the bias state holds the terminal arm in contact with moveable member 101. In an exemplary embodiment, this movement involves moving the terminal arms out of the bias position, moving the moveable member into the space occupied by the terminal arms in the bias position, and then releasing the terminal arms to create mechanical and electrical contact between the arms and moveable member 101. With reference now to FIG. 5B, terminal arms 506 and 508 are appropriately actuated to move outcroppings 510 out of the way so that moveable member 101 may be displaced as appropriate. Although this movement is shown in FIG. 5B as a rotation about a fixed pivot point 512 on terminal arms 506, 508, alternate embodiments may make use of lateral displacement in vertical and/or horizontal directions, or any other type of movement.

After the terminal arms are moved out of the bias position, moveable member 101 is appropriately actuated to place at least some portion of member 101 into the space occupied by at least some portion of terminal arms 506, 508 in the bias position. This actuation may be provided with electrostatic force as described above and below, or with any other conventional actuation techniques. In the embodiment shown in FIGS. 5A-C, moveable member 101 is laterally displaced using electrostatic force or the like so that a portion of moveable member 101 occupies space corresponding to the bias positions of outcroppings 510 of terminal arms 506, 508.

As actuating force is removed from terminal arms 506 and 508, potential energy stored in the arms is converted to kinetic energy to thereby produce a torque that attempts to return arms 506, 508 to their bias positions. Because the bias position is now occupied by moveable member 101, however, arms 506 and 508 impact upon member 101 and are suitably prevented from further movement. Because potential energy remains in the arms until they are placed in the bias position, a mechanical force is provided that maintains arms 506, 508 against moveable member 101 to thereby hold switch 500 in the closed state (corresponding to a closed circuit). Accordingly, switch 500 will remain in the closed state even though no further electrostatic or other energy is expended. Although FIGS. 5A-C have concentrated on actuation of terminal arms 506 and 508, similar concepts could be employed to actuate terminal arms 502, 504 and to place moveable member 101 in contact with arms 502, 504. Switch 500 is therefore capable of several stable output states, and may be considered to be a multi-stable switch.

Additional detail about an exemplary actuation scheme is shown in FIG. 6. With reference now to FIG. 6, each terminal arm 506, 508 is fabricated with an electrostatic-sensitive area 606 that is receptive to electrostatic energy provided by actuators 602, 604, respectively. Electrostatic energy from actuators 602, 604 appropriately attracts a metal, permalloy or other material in areas 606 to displace the arms away from their bias position. Although actuators 602, 604 and areas 606 are shown as comb-type actuators in FIG. 6, any type of electrostatic or other actuation could be used in alternate but equivalent embodiments. Similarly, moveable member 101 may be actuated into position using any actuation technique or structure 308. Although a simple block actuator 308 is shown in FIG. 6, in practice moveable member 101 may be displaced with a comb-type or other actuator such as that discussed in conjunction with FIG. 3 above.

In various embodiments, the relative positions of outcropping 510 and areas 606 may be designed so as to increase the amount of leverage applied by terminal arms 506 and/or 508 upon moveable member 101. In the embodiment shown in FIG. 6, arms 506 and 508 appropriately pivot about a relatively fixed base 512. If the actuation force is applied to the arms at a position on arms 506, 508 that is relatively far from the pivot point, the amount of displacement realized from the actuation force can be increased or maximized. Similarly, by locating outcropping 510 to be relatively nearer to pivot point 510, the amount of leverage applied by arms 506, 508 upon member 101 can be increased. This increase in leverage appropriately provides improved mechanical force to thereby maintain arms 506, 508 in position against member 101, and serves to increase the efficiency of force applied for a given duration or magnitude of actuating force. Of course other physical layouts of arms 506, 508 and member 101 could be formulated, with outcropping 510 and/or areas 606 being relocated, eliminated or combined in other equivalent embodiments. The efficiency of the actuating force can be further increased by providing a dielectric material in the spaces surrounding and/or in close proximity to actuators 602, 604 and/or areas 606. Examples of dielectric materials that may be present in various exemplary embodiments include ceramics, polymers (e.g. polyimides or epoxies), silicon dioxide ($SiO_2$), dielectric liquids and/or any other organic or inorganic dielectric material.

With reference now to FIGS. 7A and 7B, an exemplary bi-stable micro electromagnetic switch 750 suitably includes a buckling membrane 756 that provides a flexible support and connection for a moveable member 758. Actuators 752 and 760 suitably attract and/or repel membrane 756 to place contacts 754 and 758 in and out of electrical contact, and to thereby place switch 750 in closed and open states, respectively. Switch 750 is shown in an "open" state (corresponding to an open circuit) in FIG. 7A, and in a closed state (corresponding to a closed circuit) in FIG. 7B.

In an exemplary embodiment, buckling membrane 758 is a compressed beam that is capable of buckling in two or more directions to maintain switch 750 in multiple mechanically-stable states. Membrane 758 may be a double-supported beam fabricated from a substrate 102 as described above, for example, or may be fabricated from any other source using MEMS or other conventional techniques. Contacts 754 and 758 are formed of any conductive material, including gold, copper, aluminum or the like. By applying electrostatic impulses at electrodes 752 and 768, contact 758 is appropriately placed in or out of an electrical connection with contact 754. An electrostatic pulse from electrode 760, for example, attracts contact 758 toward electrode 760. Because membrane 756 is designed to buckle in a mechanically stable position, contact 756 remains positioned away from contact 754 until a suitable pulse from electrode 752 attracts contact 758 toward contact 754. In alternate embodiments, switch 750 may be designed to actuate using electrostatic repulsion, thermal actuation, piezoelectric actuation, and/or the like. Switch 750 is suitably provided in any housing 762, support or substrate as appropriate.

Any of the switches 300, 500, 600, 750 and the like described herein may be packaged using conventional wafer bonding techniques or the like. Any number of switches may be formed on a common substrate; accordingly, any number of switches may be joined in any manner and may be packaged individually or in combination. In a further embodiment, various bi- and/or tri-state switches may be joined together to create larger switch fabrics capable of simultaneously routing multiple signals between multiple inputs and/or outputs. Alternatively, multiple switches may be interconnected to form multiplexer circuits that are capable of routing signals from one or more inputs to any number of outputs. Other types of conventional switching circuits that may be formed from interconnected micro electromagnetic switches include de-multiplexers, serial-to-parallel and parallel-to-serial converters, and the like. Indeed, a wide variety of integrated and/or discrete circuits could be formulated using the various switches and techniques described herein.

With reference to FIG. 8, a conventional switch such as switch 300 described in FIGS. 3-4 above may be connected such that moveable member 101 is electrically coupled to an input source of electrical energy 814, and such that the receiving terminals 102A-B are each electrically coupled to outputs of the switch. Further, actuator 308 is appropriately connected to receive a control signal 816 from an external device, circuit or the like. Control signal 816 suitably provides electrical energy to actuator 308 to provide an electrostatic pulse or the like to actuate moveable member 101 and to thereby place switch 300 into a desired state. Accordingly, by actuating moveable member 101 between receiving terminals 102A and 102B in response to control signal 308, electrical energy and/or signals received from an input terminal 814 of the switch can be toggled between two output terminals 810 and 812. If switch 300 is bi- or tri-stable as described above, the switch will remain in the desired output state even when actuation energy is removed from switch 300, as appropriate.

Accordingly, many types of micro electromechanical switches are capable of providing enhanced electrical connectivity, and are capable of remaining in a selected output state even when actuation energy is no longer provided to the switch. Such switches have numerous applications across many fields, including medical, aerospace, consumer electronics, and the like.

In particular, a "smart lead" may be created to improve the flexibility and accuracy of electrostimulation to a heart or other part of the human body, or to improve sensing of a parameter in the heart or other body part. Previous attempts to provide electrical stimulation or other signals from a single source to multiple destinations within the body typically required signal "splitting" whereby the input signal was simultaneously provided to multiple output destinations. By incorporating switches such as those described above, however, electrostimulation can be applied in a much more accurate manner. By routing signals from an input source to a single destination (or to a discrete set of destinations), the accuracy and programmability of electrostimulation is greatly improved, thereby improving treatment of the patient. Similarly, improved sensors can be fabricated using switching leads. Electrical sensors, for example, can be formulated to allow switching of signals from multiple sensor locations to one or more receivers. Several types of smart leads described herein include Y-adapters, switch arrays, and the like.

A wide variety of switchable leads for electrostimulation, sensing and other applications may be fabricated in any manner. In various exemplary embodiments, switching leads may be used to implement multiplexing (e.g. many-to-one) and/or demultiplexing (e.g. one-to-many) functionality. Switches used in active leads may be controlled by any source, such as an implantable medical device, external programming device, magnetic device, telemetry device and/or the like as described more fully below. Similarly, switched leads may receive electrical power from any source such as a battery, from applied control or data signals, from an external radiated source (e.g. any source of optical, electromagnetic, acoustic or other energy), from an external power source (e.g. from an IMD or other power source coupled to the lead), or from any other source. In various exemplary embodiments, active leads receive electrical power via a lead connection to an implantable medical device.

With reference to FIG. 9, an exemplary smart lead Y-adapter 700 suitably includes an input lead 706, a switching section 708 and two or more output leads 710, 712. Each output lead 710, 712 may provide an interface to another conduction device (e.g. a cable or the like) or may terminate with an electrode 714, 716 as appropriate for providing electrical energy to a heart 720 or other organ in a human or mammalian body. Input lead 706 suitably provides electrical energy and/or signals from an input source to switching section 708. In an exemplary embodiment, input lead 706 has a coupler 704 suitable for connecting to a plug 702 on an output lead from a stimulator such as a pacing device, implantable medical device (IMD), implantable pulse generator (IPG), pacemaker, defibrillator, heart monitor or the like. Plug 702 and coupler 704 may be conventional IS-1 connectors, for example. Alternatively, input lead 706 may interface with any other source of electrical energy that is internal or external to the patient using any conventional coupling or interface devices or techniques.

Switching section 708 is any circuit or device capable of toggling electrical signals received on input lead 706 between output leads 714 and 716. In an exemplary embodiment, switching section 708 includes one or more multi-stable micro electromechanical switches such as the switches described above. With momentary reference again to FIG. 8, input terminal 814 of one or more switches is appropriately connected to input lead 706, and output terminals 710, 712 of one or more switches are ultimately connected to output leads 710 and/or 712. Toggling between the two output states is accomplished by providing an appropriate control signal 816 to actuator 308 to actuate moveable member 101 as desired. Referring back to FIG. 8, electrical signals by an IMD or other source connected to input lead 706 are therefore toggled between output leads 710 and 712. Control signal 816 may be provided by the same source as the input electrical energy, or may be provided by a physician or other external source using telemetry or another communications technique, as described more fully below.

In various equivalent embodiments, Y-adapter 700 is used to provide monitoring signals from heart 720 to a monitoring device (e.g. the CHRONICLE products available from Medtronic Inc. of Minneapolis, Minn.). Accordingly, leads 714 and/or 716 may be thought of as "input" leads in some embodiments, and lead 706 may be similarly thought of as an "output" lead in embodiments wherein electrical signals are provided from heart 720 to a receiving device. Similarly, leads having any number of inputs and/or outputs may be fabricated by inter-connecting one or more switches or by any other technique. In various embodiments, multiplexing and/or de-multiplexing functions allow switching between any number of inputs and any number of outputs. Further, embodiments that allow simultaneous activation of a subset of input and/or output leads could be formulated. Such embodiments might allow simultaneous activation of two leads from a set of eight, for example, wherein the signals transmitted on the two active leads may be identical or different from each other. In a "dual lead multiplexer", for example, two or more separate input leads carrying different electrical signals arrive at the adapter, and each of the signals can be dispatched to two or more different output leads departing from the adapter. Accordingly, a wide range of equivalent embodiments could be formulated.

With reference now to FIG. 10, an exemplary switchable electrode array 900 suitably includes an epicardial electrode array or matrix with multiple electrode tips 910 housed within a common carrier 912. Carrier 912 may be connected to any type of input lead 706, such as a conventional bipolar lead-body or the like. Input lead 706 may be fitted with a connector 704 (e.g. an IS-1 connector or the like) for connection to an IMD or other stimulator, as described above. Array 900 may be placed at the epicardium using minimally invasive tools or the like.

The particular electrode tip(s) 910 that become active at any time may be determined by a switch fabric 908 that appropriately couples electrical signals from input lead 706 to the various electrode tips 910. In operation, switch fabric 908 includes any number of switches as appropriate to toggle the active and inactive states of the various electrodes 910.

In practice, multiple switches and/or types of switches may be wired in any combination to implement a wide variety of switching logic. Each of the various switches may be formed on a common substrate (as shown, for example, in FIG. 3), and/or may be housed in a common package. With reference to FIG. 11, an exemplary switching scheme for implementing a 1×4 switchable electrode array is shown, although switch fabrics of any dimensions (e.g. 2×16, 1×8 and the like) may be fabricated in alternate embodiments. In the embodiment shown in FIG. 11, four switches 1002, 1004, 1006 and 1008 are shown wired in a tree structure such that an input signal provided to switch 1002 can be provided to any of the electrodes 910 in array 912. Each of the switches may be double-throw switches 300 such as those shown in FIGS. 3-4 above. Alternatively, single throw switches 750 such as those shown in FIGS. 7A-B could be used in an alternate embodiment, although more of such switches may be required to implement similar logic.

In operation, each of the various switches 1002,1004,1006 and 1008 are placed into a desired state by control signals 1012 (which may correspond to control signals 816 described above) provided by control circuit 1010. Control circuit 1010 may receive control instructions from any source, such as from an optional telemetry antenna 1014, from an IMD or other device that provides input electrical signals, or from any other source. In an exemplary embodiment, control instructions are multiplexed or otherwise coded by an IMD or other source and transmitted to control circuit 1010 via input lead 706. Alternatively, control instructions may be provided from a wireless device such as telemetry-based programming unit. An example of an external programming unit that operates using radio frequency (RF) encoded signals is described in commonly-assigned U.S. Pat. No. 5,312,453. Another exemplary programming device is the Medtronic Model 9790 programmer, although any device or technique could be used to provide control information in alternate embodiments. The desired active electrodes may be selected at implant and may remain relatively unchanged over the duration of operation, or may be altered during operation in response to physician instructions, monitored physical conditions of the patient, and/or any other factors.

While at least one exemplary embodiment has been presented in the foregoing detailed description, it should be appreciated that a vast number of variations exist. The concept of actuating a switch between several states in response to a control signal may be applied to any type of micro electromechanical or other switch, for example, and is not limited to the particular switches described herein. Similarly, the various medical devices and other applications described herein are not limited by the particular switches described herein, but may be implemented with a wide variety of equivalent switches and other components. Further, although the various devices are frequently described with reference to a human heart, various equivalent embodiments could be used to apply electrostimulation to other parts of the body (e.g. for neurostimulation) and/or could be used in non-human mammals. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. An apparatus for multiplexing electrical energy from an implantable medical device to either of first and second locations on a human heart, the apparatus comprising:

an input lead configured to electrically interface with the implantable medical device;

a first output lead for coupling to a first heart location to provide electrical energy to the first heart location;

a second output lead for coupling to a second heart location to provide electrical energy to the second heart location; and a Y-adapter coupled to the input lead and the first and second output leads, the Y-adapter including:

a bi-stable switching circuit capable of toggling electrical signals received on the input lead from the implantable medical device between the first and second output leads in response to a control signal, and a control circuit to receive control instructions from a source and produce the control signal, the bi-stable switching circuit including a micro electromechanical switch having an input terminal electrically coupled to the input lead, having a first output terminal coupled to the fast output lead, and a second output terminal coupled to the second output lead, a movable member coupled to the input terminal, and an actuator coupled to the control circuit and generating an electrostatic force in response to the control signal, wherein the movable member is displaced to electrically engage one of the first output terminal and the second output terminal in response to a generation of the electrostatic force, wherein the movable member is mechanically biased to maintain the electrical engagement of the movable member wit said one of the first output terminal and the second output terminal after the control signal is terminated, wherein the movable member toggles through a subsequent displacement to electrically engage the other one of the first output terminal and the second output terminal in response to a subsequent generation of the electrostatic force, and wherein the movable member is mechanically biased to maintain the electrical engagement of the movable member with said other one of the first output terminal and the second output terminal after the control signal is terminated, and wherein the movable member is electrically engaged with the first output terminal in a first state and the movable member is electrically engaged wit the second output terminal in a second state.

2. The apparatus of claim 1 wherein the control circuit receives control instructions from the implantable medical device.

3. The apparatus of claim 1 wherein the control circuit includes a telemetry circuit to receive control instructions.

4. The apparatus of claim 1 wherein at least one of the first and second output leads includes an electrode array.

5. The apparatus of claim 1 wherein the movable member comprises a buckling membrane.

6. The apparatus of claim 1 wherein the switch comprises a multi-stable switch wherein the movable member is electrically engaged with the first output terminal in a first state, the movable member is electrically engaged with the second output terminal in a second state, and the movable member is not electrically engaged with the first output terminal and the second terminal in a third state.

7. The apparatus of claim 1 wherein the switch is a micro electromechanical switch formed on a substrate, and wherein the movable member and the first and second output terminals each comprise:

an insulating layer proximate to the substrate; and a conducting layer proximate to the insulating layer opposite the substrate;

and wherein the conducting layers of the moveable member and first and second output terminals each comprise a protruding region tat extends outward from the conducting layer in a plane occupied by the conducting layer and parallel to the substrate, and the protruding region of the moveable member is configured to switchably engage the protruding region of the first and second output terminals to form electrical connections therebetween.

8. The apparatus of claim 1 wherein the switch is a multi-stable electromechanical switch comprising:

a first pair of receiving terminals corresponding to the first output terminal and a second pair of receiving terminals corresponding to the second output terminal, wherein each of the first and second pair of receiving terminals are mechanically biased to a bias position corresponding to an open stale, and wherein each terminal of the first and second pair of receiving terminals is configured to interface with the moveable member in the closed state; and wherein the actuator is configured to provide electrostatic force to thereby displace the at least one of the first and second pairs of receiving terminals from the bias position, and to displace the moveable member toward the bias position;

wherein each of the first and second pairs of receiving terminals are further configured to return toward the bias position when the electrostatic force_is removed, and to thereby create an electrical connection with the moveable member, thereby retaining the electromechanical switch in a desired stale.

* * * * *

UNITED STATES PATENT AND TRADEMARK OFFICE

CERTIFICATE OF CORRECTION

PATENT NO. : 7,474,923 B2
APPLICATION NO. : 10/425527
DATED : January 6, 2009
INVENTOR(S) : Houben et al.

It is certified that error appears in the above-identified patent and that said Letters Patent is hereby corrected as shown below:

Col. 13, line 35, delete “wit” and insert in place thereof -- with --;

Col. 13, line 50, delete “wit” and insert in place thereof -- with --;

Col. 14, line 38, delete “stale” and insert in place thereof -- state --;

Col. 14, line 45, delete “tion.” and insert in place thereof -- tion, --.

Signed and Sealed this

First Day of September, 2009

David J. Kappos
*Director of the United States Patent and Trademark Office*